(12) United States Patent
Bel-Rhlid

(10) Patent No.: US 11,541,025 B2
(45) Date of Patent: Jan. 3, 2023

(54) METHOD OF PREPARING A COMPOSITION COMPRISING FERULIC ACID

(71) Applicant: SOCIETE DES PRODUITS NESTLE S.A., Vevey (CH)

(72) Inventor: Rachid Bel-Rhlid, Savigny (CH)

(73) Assignee: Societe des Produits Nestle S.A., Vevey (CH)

( * ) Notice: Subject to any disclaimer, the term of this patent is extended or adjusted under 35 U.S.C. 154(b) by 366 days.

(21) Appl. No.: 16/603,301

(22) PCT Filed: Apr. 3, 2018

(86) PCT No.: PCT/EP2018/058444
§ 371 (c)(1),
(2) Date: Oct. 7, 2019

(87) PCT Pub. No.: WO2018/188987
PCT Pub. Date: Oct. 18, 2018

(65) Prior Publication Data
US 2020/0054590 A1    Feb. 20, 2020

(30) Foreign Application Priority Data
Apr. 10, 2017   (EP) .................................. 17165796

(51) Int. Cl.
| | | |
|---|---|---|
| A61K 31/192 | (2006.01) |
| A23L 33/195 | (2016.01) |
| A23L 7/10 | (2016.01) |
| A23L 33/105 | (2016.01) |
| A61P 3/04 | (2006.01) |
| A61P 3/10 | (2006.01) |
| A61K 9/00 | (2006.01) |

(52) U.S. Cl.
CPC ............ *A61K 31/192* (2013.01); *A23L 7/115* (2016.08); *A23L 33/105* (2016.08); *A23L 33/195* (2016.08); *A61K 9/0053* (2013.01); *A61P 3/04* (2018.01); *A61P 3/10* (2018.01); *A61K 2236/331* (2013.01)

(58) Field of Classification Search
CPC .................................................... A61K 31/192
See application file for complete search history.

(56) References Cited

U.S. PATENT DOCUMENTS

2009/0221039 A1*  9/2009  Record ................ C12N 9/0061
                                                                  435/69.7

FOREIGN PATENT DOCUMENTS

| CN | 103805639 A | 5/2014 | | |
|---|---|---|---|---|
| JP | 54095760 A | 7/1979 | | |
| JP | 2004236634 | 8/2004 | | |
| JP | 2012514989 A | 7/2012 | | |
| JP | 2013063957 A | 4/2013 | | |
| JP | 2013529475 A | 7/2013 | | |
| WO | 2008008793 | 1/2008 | | |
| WO | 2016162227 | 10/2016 | | |
| WO | WO2016/16227 | * 10/2016 | ........... A61K 31/192 |

OTHER PUBLICATIONS

Handbook for Examination of Patents and Utility Models, Part II, Chapter 2, 56 pages.
Japan Patent Office Communication for Application No. P2019-551933, Dispatch No. 859105, Dispatch Date Dec. 21, 2021, 10 pages.
Japanese Office Action for Patent Application No. P2019-551933 dated Apr. 5, 2022.

* cited by examiner

Primary Examiner — Paul V Ward
(74) Attorney, Agent, or Firm — K&L Gates LLP

(57) ABSTRACT

The present invention relates to a method of preparing a composition comprising ferulic acid. An aspect of the invention is a composition comprising hydrolysed wheat bran for use in the treatment or prevention of metabolic disease.

14 Claims, 1 Drawing Sheet

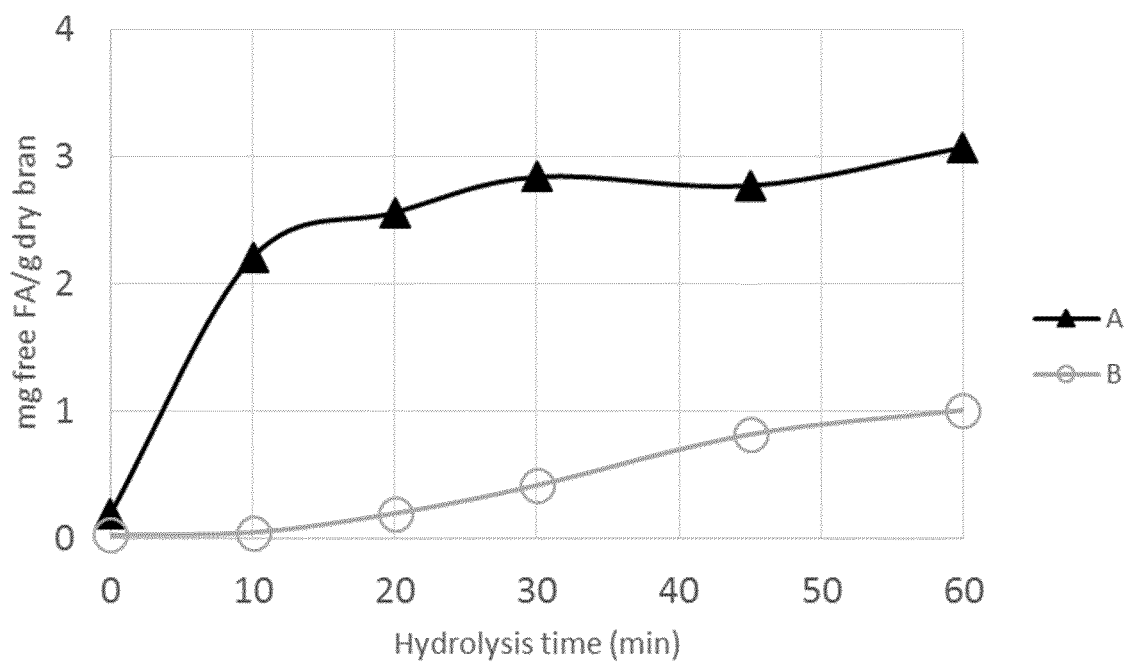

METHOD OF PREPARING A COMPOSITION COMPRISING FERULIC ACID

CROSS REFERENCE TO RELATED APPLICATIONS

The present application is a National Stage of International Application No. PCT/EP2018/058444, filed on Apr. 3, 2018, which claims priority to European Patent Application No. 17165796.8, filed on Apr. 10, 2017, the entire contents of which are being incorporated herein by reference.

FIELD OF THE INVENTION

The present invention relates to a method of preparing a composition comprising ferulic acid. An aspect of the invention is a composition comprising hydrolysed wheat bran for use in the treatment or prevention of metabolic disease.

BACKGROUND OF THE INVENTION

Bran, which along with germ, is an integral part of whole grains, is composed of a wide range of compounds with potential health benefits (fibres, vitamins, minerals, and phytochemicals). Ferulic acid (FA) is a component of bran which is known to have many physiological functions. However, FA is mostly bound to cell wall polysaccharides and so its bioavailability in bran is very low. Faulds [C. B. Faulds et al., Appl. Microbiol. Biotechnol., 64: 644-650 (2004)] describes a process of obtaining FA from wheat bran involving destarching the bran by alcohol extraction and then treating the non-soluble fraction with feruloyl esterases and glycosyl hydrolases from *Humicola insolens*. The reaction time was 3 hours. Without alcohol extraction only 0.5 mg/g of FA was released, but with alcohol extraction the release was 2.88 mg/g.

It would be advantageous to be able to provide an improved method for releasing FA from bran, ideally avoiding the need for an alcohol extraction step. It would be advantageous to provide a method of releasing FA which could be applied in-process during food production using ingredients from natural sources.

SUMMARY OF THE INVENTION

An object of the present invention is to improve the state of the art and to provide an improved method to overcome at least some of the inconveniences described above or at least to provide a useful alternative. The object of the present invention is achieved by the subject matter of the independent claims. The dependent claims further develop the idea of the present invention. Any reference to prior art documents in this specification is not to be considered an admission that such prior art is widely known or forms part of the common general knowledge in the field. As used in this specification, the words "comprises", "comprising", and similar words, are not to be interpreted in an exclusive or exhaustive sense. In other words, they are intended to mean "including, but not limited to".

Accordingly, the present invention provides in a first aspect a method of preparing a composition comprising ferulic acid, the method comprising the steps of; forming a bran mixture comprising bran and water, the mixture having a water content of at least 50 wt. % and comprising from 1 to 50% by weight of bran; heating the bran mixture to a temperature of between 80 and 150° C.; cooling the bran mixture to below 50° C. and; subjecting the bran mixture to an enzymatic treatment comprising contacting the bran mixture with a carbohydrase and a feruloyl esterase. A further aspect of the invention relates to a composition comprising hydrolysed wheat bran for use in the treatment or prevention of metabolic disease or obesity wherein the composition comprises between 0.001 and 0.25 wt. % ferulic acid.

It has been surprisingly found by the inventors that a thermal pre-treatment of bran before applying enzymes results in a much higher release of FA, for example the release of FA may be three times greater with thermal pre-treatment using the same enzymatic treatment. The thermal pre-treatment also increases the production of low molecular weight soluble fibres and free amino acids which are contribute to a positive nutritional profile. In addition, the thermal pre-treatment improves the processability of the bran. It pre-gelatinizes the starch and inactivates endogenous enzymes which may be present in the bran.

BRIEF DESCRIPTION OF THE DRAWINGS

FIG. 1 shows the release of ferulic acid (mg free ferulic acid/g dry bran) over time (minutes) during hydrolysis of a slurry of wheat bran with application of thermal pre-treatment (A) and without (B).

DETAILED DESCRIPTION OF THE INVENTION

Consequently the present invention relates in part to a method of preparing a composition comprising ferulic acid, the method comprising the steps of; a) forming a bran mixture comprising bran and water, the mixture having a water content of at least 50 wt. % (for example at least 70 wt. %, for further example between 75 wt. % and 90 wt. %) and comprising from 1 to 50% by weight of bran (for example comprising from 1 to 30% by weight of bran, for further example comprising between 20 and 30% by weight of bran); b) heating the bran mixture to a temperature of between 75 and 150° C. (for example between 80 and 120° C., for further example between 85 and 115° C.); c) cooling the bran mixture to below 50° C. (for example to between 10 and 50° C., for further example to between 35 and 45° C.) and; d) subjecting the bran mixture to an enzymatic treatment comprising contacting the bran mixture with a carbohydrase and a feruloyl esterase.

Ferulic acid, or (E)-3-(4-hydroxy-3-methoxy-phenyl)prop-2-enoic acid is a hydroxycinnamic acid found in the seeds of coffee, apple, artichoke, peanut, and orange, as well as in both seeds and cell walls of plants such as rice, wheat and oats.

The bran according to the method of the invention may be derived from the major cereals consumed worldwide: wheat, buckwheat, rice, maize, barley, oats, rye, millet, and sorghum. In one embodiment, the bran is selected from rice bran, wheat bran, oat bran, and combinations thereof; preferably the bran is wheat bran. The bran may be comprised within a whole grain. Whole grains are cereal grains that contain the germ, endosperm, and bran. The whole grain may be a ground whole grain. Bran is a popular food ingredient with good consumer acceptability and nutritional value.

Heating the bran mixture according to step b of the method of the invention may, for example, be performed for a duration of at least 10 seconds. Heating the bran mixture according to step b of the method of the invention may, for example, be performed at a temperature of between 75 and 100° C. for a duration of between 2 and 20 minutes. Heating the bran mixture according to step b of the method of the invention may be performed by direct steam injection, the bran mixture having steam injected into it. The bran mixture may, for example, be heated to a temperature between 100 and 130° C. for a duration of between 10 seconds and 2 minutes.

The enzymatic treatment according to the method of the invention may comprise contacting the bran mixture with a carbohydrase such as xylanase and a feruloyl esterase. The bran mixture may be contacted with a carbohydrase (such as xylanase) and feruloyl esterase in the form of a mixture of a carbohydrase and feruloyl esterase or the bran mixture may be contacted with carbohydrase and feruloyl esterase sequentially. Mixtures comprising carbohydrase and feruloyl esterase enzymes are available commercially. Commercial enzyme preparations generally contain a mixture of enzymes, the mixture having main functionalities as well as side activities. In an embodiment of the method of the invention the bran mixture may be contacted with a commercial enzyme preparation comprising both xylanase and feruloyl esterase, for example an enzyme preparation selected from the group consisting of Depol™ 740L as sold by Biocatalysts, Pentopan® 500BG as sold by Novozymes, Ultraflow L as sold by Novozymes, Depol™ 453P as sold by Biocatalysts and chlorogenate esterase as sold by Kikkoman. In an embodiment of the method of the invention the bran mixture may be contacted with a carbohydrase and a feruloyl esterase in the form of a mixture of an enzyme preparation selected from the group consisting of Depol™ 740L as sold by Biocatalysts, Pentopan® 500 BG as sold by Novozymes, Ultraflow L as sold by Novozymes, Depol™ 453P as sold by Biocatalysts and chlorogenate esterase as sold by Kikkoman and an enzyme preparation selected from the group consisting of Depol™ 761L as sold by Biocatalysts, Grindamyl™ Powerbake 900 as sold by Danisco, Depol™ 453P as sold by Biocatalysts, Pentopan® Mono BG as sold by Novozymes, Validase™ X as sold by Valley Research, Depol™ 333P as sold by Biocatalysts and Celluclast® BG as sold by Novozymes. The bran mixture may be contacted with a carbohydrase and a feruloyl esterase in the form of a mixture of Pentopan® 500 BG as sold by Novozymes and Validase™ X as sold by Valley Research. The bran mixture may be contacted with Pentopan® 500BG as sold by Novozymes. Although Pentopan® 500 BG is primarily considered to be a multi-component xylanase, it also has feruloyl esterase activity.

The bran in the bran mixture according to the method of the invention may be comprised within a whole grain cereal. The whole grain may be obtained from different sources. Examples of whole grain sources are semolina, cones, grits, flour and micronized grain (micronized flour). The whole grains may be ground, preferably by dry milling. Whole grains are cereals of monocotyledonous plants of the Poaceae family (grass family) cultivated for their edible, starchy grains. Examples of whole grain cereals include barley, rice, black rice, brown rice, wild rice, buckwheat, bulgur, corn, millet, oat, sorghum, spelt, triticale, rye, wheat, wheat berries, teff, canary grass, Job's tears and fonio. Plant species that do not belong to the grass family also produce starchy seeds or fruits that may be used in the same way as cereal grains, are called pseudo-cereals. Examples of pseudo-cereals include amaranth, buckwheat, tartar buckwheat and quinoa. When designating cereals, this will include both cereal and pseudo-cereals.

The bran mixture according to the method of the invention may be formed by enzymatic hydrolysis of a whole grain cereal with an alpha-amylase, said alpha-amylase showing no hydrolytic activity towards dietary fibres when in the active state. The term "no hydrolytic activity towards dietary fibres" may encompass up to 5% degradation of the dietary fibres, such as up to 3%, such as up to 2% and such as up to 1% degradation. Such degradation may be unavoidable if high concentrations or extensive incubation times are used. Treating a whole grain cereal with an alpha-amylase causes it to become less viscous and more suitable for inclusion into a wide range of food products.

By using an alpha-amylase showing no hydrolytic activity towards dietary fibres the bran component of the whole grain cereal is retained.

The bran mixture may be formed by a process comprising the steps; a) contacting a whole grain component with an enzyme composition in water, the enzyme composition comprising at least one alpha-amylase, said enzyme composition showing no hydrolytic activity towards dietary fibres and, b) allowing the enzyme composition to react with the whole grain component to provide a bran mixture in the form of a whole grain hydrolysate. The enzyme composition comprising at least one alpha-amylase may additionally comprise a protease. As described in WO201276051, amylases such as Validase HT 425L (Valley Research) and proteases such as Alcalase 2.4L (Novozymes) show no hydrolytic activity on either beta-glucan or arabinoxylan.

The bran mixture according to the method of the invention may be heated to a temperature of between 100 and 150° C. after being subjected to the enzymatic treatment comprising contacting the bran mixture with a carbohydrase and a feruloyl esterase. For example the bran mixture may be heated to a temperature of between 100 and 150° C. by direct steam injection.

The bran mixture according to the method of the present invention may be dried after being subjected to the enzymatic treatment comprising contacting the bran mixture with a carbohydrase and a feruloyl esterase. For example the bran mixture may be dried by roller drying.

The bran according to the method of the invention may have a particle size distribution D90 of less than 500 μm. The inventors found that a particle size distribution D90 of greater than 500 μm led to problems of processing such as phase separation. A D90 value is the diameter below which lie 90% of the particles in the distribution. The particle size may for example be measured by laser light scattering.

The enzymatic treatment comprising contacting the bran mixture with a carbohydrase and a feruloyl esterase according to the method of the invention may be performed at a temperature between 30 and 50° C., for example between 35 and 45° C. The enzymatic treatment comprising contacting the bran mixture with a carbohydrase and a feruloyl esterase according to the method of the invention may be performed for a duration of between 10 minutes and 4 hours, for example between 30 minutes and 3 hours, for further example between 90 minutes and 150 minutes. It should be understood that the method of the invention may be performed as a batch process or a continuous process. When the method is a continuous process the duration of the enzymatic treatment is the average residence time for which the bran mixture is contacted with the carbohydrase and the feruloyl esterase.

The carbohydrase and/or feruloyl esterase enzymes according to the method of the invention may be comprised within a fermentation broth or an extract of a fermentation broth wherein micro-organisms in the fermentation broth have produced carbohydrase and/or feruloyl esterase enzymes. The enzymatic treatment of step d according to the method of the invention may be performed by micro-organisms. For example, the bran mixture may be fermented with micro-organisms which produce carbohydrase and/or feruloyl esterase enzymes. The micro-organisms may be selected from the group consisting of bacteria, yeast and fungi. Bacteria may for example be selected from the group consisting of *Bacillus* sp. (e.g. *B. subtilis, B. circulans, Bifidobacterium* sp. (e.g. *B. longum, B. lactis*), *Micrococcus* sp. and *Lactobacillus* sp. (e.g. *L. johnsonii*). Yeast may for example be *Streptomyces* sp. (e.g. *S. Viridisporus* or *S. Chattanoogensis*). Fungi may for example be *Aspergillus* sp., (e.g. *A. niger, A. sojae, A. nidulans* or *A. oryzae*).

The bran mixture according to the method of the invention may be mixed or assembled with a food ingredient after being subjected to the enzymatic treatment. For example, the bran mixture, after being subjected to the enzymatic treatment, may be mixed with a food ingredient during further processing into a beverage, dairy product, petfood, or food supplement.

In another aspect, the invention provides a composition comprising hydrolysed wheat bran for use in the treatment or prevention of metabolic disease or obesity wherein the composition comprises between 0.001 and 0.25 wt. % ferulic acid, for example between 0.01 and 0.15 wt. % ferulic acid, for example between 0.02 and 0.1 wt. % ferulic acid, for further example between 0.05 and 0.09 wt. % ferulic acid. The composition according to the present invention is to be provided to a subject. In an embodiment, the subject is a mammal, such as a human, a cat, a dog or a horse. The invention may provide the use of a composition comprising hydrolysed wheat bran for the manufacture of a medicament for the treatment or prevention of metabolic disease or obesity wherein the composition comprises between 0.001 and 0.25 wt. % ferulic acid.

In a further aspect, the invention provides a composition comprising hydrolysed wheat bran for use in the treatment or prevention of metabolic disease or obesity wherein the composition is administered to provide a dose of between 0.3 and 3.0 mg/kg body weight per day ferulic acid, for example between 0.4 and 2.0 mg/kg body weight per day ferulic acid, for further example between 0.6 and 1.0 mg/kg body weight per day ferulic acid. The ferulic acid is particularly beneficial at such doses. Preferably all the ferulic acid in the composition is provided as hydrolysed bran, for example hydrolysed wheat bran. Bran hydrolysed according to the method of the invention contains high levels of free amino acids and low molecular weight soluble fibres and so provides good nutrition. The invention may provide the use of a composition comprising hydrolysed wheat bran for the manufacture of a medicament for the treatment or prevention of metabolic disease or obesity wherein the composition is administered to provide a dose of between 0.3 and 3.0 mg/kg body weight per day ferulic acid. In a further aspect, the invention provides a composition obtained (for example obtainable) by the method of the invention for use in the treatment or prevention of metabolic disease or obesity. The invention may provide the use of a composition obtained (for example obtainable) by the method of the invention for the manufacture of a medicament for the treatment or prevention of metabolic disease or obesity.

The metabolic disease to be treated or prevented in an aspect of the invention may be selected from the group consisting of diabetes, hyperlipidemia, hypertension and cardiovascular disease. For example the metabolic disease may be type II diabetes.

The composition according to the invention may have been dried, for example it may have been roller dried. The composition for use according to the invention may be combined with an excipient. For example, the composition for use according to the invention may be combined with an excipient and formed into a pressed tablet or filled into a capsule.

The composition for use according to the invention may form part of a food product. Thus, in one aspect the invention relates to a food product comprising the composition according to the invention. In yet an aspect the invention relates to a composite food product, wherein at least one part of the composite food products comprises the composition according to the invention. This may be the case where a food product is constituted of multiple independent parts (composite), where e.g. only one of the parts comprises the composition according to the invention.

The food product, of which the composition according to the invention may form part, may be selected from the group consisting of beverages, dairy products, cereal products, petfood, and food supplements. Examples of beverages according to the present invention are meal replacements, oral nutritional supplements or ready-to-drink beverages supplemented with hydrolyzed whole grain. The dairy products according to the present invention may be powdered milk products, for example a powdered milk product comprising milk powder, ferulic acid and optionally vitamins and minerals. The dairy products according to the present invention may be fermented milk products such as yoghurts. In the context of the present invention the term yoghurt may include, but is not limited to, materials complying with local food labelling regulations concerning the term "yoghurt". Examples of cereal products according to the present invention may be selected from the group consisting of breakfast cereals, porridges, paps and cereal bars. The food product may be a powdered milk product comprising cereal, for example an instant porridge. Examples of petfood according to the present invention may be selected from the group consisting of kibbles and pellets. A food supplement, also known as a nutritional supplement or dietary supplement, is a preparation intended to supplement the diet and provide nutrients, such as vitamins, minerals, fibre, fatty acids, or amino acids that may be missing or may not be consumed in sufficient quantities in a person's diet. Examples of the form of food supplements according to the present invention are capsules and pills.

The composition of the invention may be used for weight management, for example as a dietary supplement.

The composition of the invention may be administered via enteral administration, preferably orally.

Those skilled in the art will understand that they can freely combine all features of the present invention disclosed herein. In particular, features described for the method of the present invention may be combined with the compositions of the present invention and vice versa. Further, features described for different embodiments of the present invention may be combined. Where known equivalents exist to specific features, such equivalents are incorporated as if specifically referred to in this specification. Further advantages and features of the present invention are apparent from the non-limiting examples.

EXAMPLES

Example 1: Wheat Bran Hydrolysis

Wheat bran (Provimi Kliba) was suspended in water at a total solids content of 20-23%. The suspension was then hydrolysed at 65° C. for an hour in the presence of 0.5%

Pentopan® 500 BG (Novozymes). Samples of the wheat bran were taken during the process and analysed. In previous trials, 65° C. had been found to be the highest optimal temperature before the enzyme became partially inactivated.

The effect of pre-treating the suspension at 90° C. for 10 minutes before hydrolysis was examined by repeating the process as above but adding a heating step using direct steam injection. After the heating step the suspension was cooled before hydrolysis. FIG. 1 shows that the thermal pre-treatment (A) increases the ferulic acid release by almost a factor of three over the sample without pre-treatment (B). The enzymatic treatment also increased the content of low molecular weight soluble fibres from 3% to 9% on a dry bran basis.

The invention claimed is:

1. A method of preparing a composition comprising ferulic acid, the method comprising:
    forming a bran mixture comprising bran and water, the bran mixture having a water content of at least 50 wt. % and comprising from 1 to 50% by weight of bran;
    heating the bran mixture to a temperature of between 75 and 150° C.;
    cooling the bran mixture to below 50° C.; and
    subjecting the bran mixture to an enzymatic treatment comprising contacting the bran mixture with a carbohydrase and a feruloyl esterase.

2. The method according to claim 1, wherein the bran mixture is heated by direct steam injection.

3. The method according to claim 2, wherein the bran mixture is formed by enzymatic hydrolysis of a whole grain cereal with an alpha-amylase, the alpha-amylase showing no hydrolytic activity towards dietary fibers when in an active state.

4. The method according to claim 1, wherein the bran mixture is heated to a temperature of between 100 and 150° C. after being subjected to the enzymatic treatment.

5. The method according to claim 1, wherein the bran mixture is dried after being subjected to the enzymatic treatment.

6. The method according to claim 1, wherein the bran has a particle size distribution D90 of less than 500 µm.

7. The method according to claim 1, wherein the enzymatic treatment is performed at a temperature between 30 and 50° C.

8. The method according to claim 1, wherein the bran is wheat bran.

9. The method according to claim 1, wherein the enzymatic treatment is performed by micro-organisms.

10. The method according to claim 1, wherein the bran mixture is mixed or assembled with a food ingredient after being subjected to the enzymatic treatment.

11. A method for treating metabolic disease or obesity, the method comprising administering a composition comprising hydrolysed wheat bran to an individual in need thereof, the composition comprising between 0.001 and 0.25 wt. % ferulic acid.

12. The method according to claim 11, wherein the metabolic disease or obesity is selected from the group consisting of type II diabetes, and cardiovascular disease.

13. The method in accordance with claim 11, wherein the composition is to be administered orally.

14. The method in accordance with claim 11, wherein the composition is to be administered in a daily dose of between 0.30 and 3.0 mg/kg body weight per day ferulic acid.

* * * * *